William R. Gardner.

Improvement in Pessaries.

4291

REISSUED MAR 7 1871

Witnesses

Chas. H. Smith

Geo. D. Walker.

William R. Gardner,

Lemuel W. Serrell.

Attys.

United States Patent Office.

WILLIAM R. GARDNER, OF LEONARDSVILLE, NEW YORK.

Letters Patent No. 105,191, dated July 12, 1870; reissue No. 4,291, dated March 7, 1871.

IMPROVEMENT IN PESSARIES.

The Schedule referred to in these Letters Patent and making part of the same.

*To all whom it may concern:*

Be it known that I, WILLIAM R. GARDNER, of Leonardsville, in the county of Madison and State of New York, have invented an Improvement in Pessaries; and the following is declared to be a correct description of the same.

My improved pessary is made with an opening at one end, with two flaring lips of a bottomless cup for the reception of the posterior and anterior surfaces of the lips and neck of the uterus, and at the other end the pessary is curved to rest upon the pubic bone.

To facilitate the insertion of the pessary the cup is made in two parts, hinged together, so as to be closed as the instrument is inserted.

In the drawing—

The portion *a* of the pessary forms a frame or lever, the curved end *b* of which sits upon the pubic bone The cup-shaped support is formed of the flaring lips *c d*.

Figure 1:
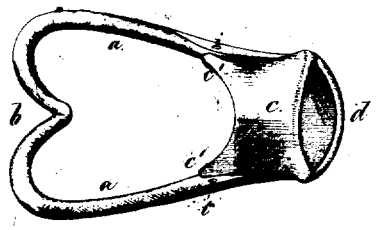
Figure 1 is a top view of the pessary, as closed, ready for insertion.
Figure 3:
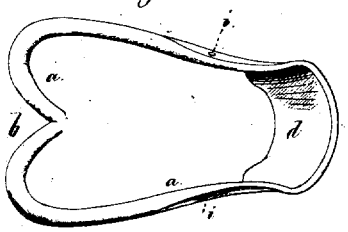
Figure 3 represents the frame, with the movable section of the cup removed.
Figure 2:
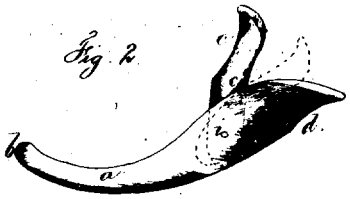
Figure 2 is a side view.
Figure 4:
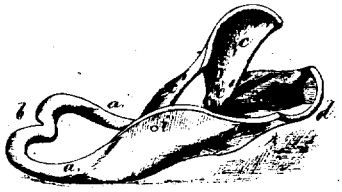
Figure 4 is a perspective view.

The lip *c* is shown with the arms or extension sides *c'* reaching to the joint-pins *i i*, a limited movement being allowed so that the parts can be closed, as indicated by the dotted lines in fig. 2, or opened to form a bottomless cup.

When closed the pessary can be easily passed through the vulva, and then opened by a proper movement of the finger and adjusted to the posterior and anterior surfaces of the lips and neck of the uterus, to firmly secure it in position by resting the end *b* of the pessary against the inner surface of the pubic bone.

The pessary affords a complete support for the uterus, and effectually controls cases of antiversion, antiflexion, retroversion, retroflexion and prolapsus of the uterus.

In pessaries made with the flaring lips *a b* there are notches or depressions between said lips, so that the pessary will not be liable to become displaced because the neck of the uterus spreads into these spaces.

I claim as my invention—

1. The pessary, made with the lips *c* and *d* and intermediate notches upon a bottomless cup, for receiving the lips and neck of the uterus, in combination with the curved end *b* for resting upon the pubic bone, substantially as specified.

2. The lips *c* and *d* of the bottomless cup, united by the hinge *i*, in combination with the frame *a b*, substantially as and for the purposes set forth.

Signed this 12th day of October, A. D. 1870.

W. R. GARDNER.

Witnesses:

DENNIS HENDIN,

N. BRAND.